(12) United States Patent
Van Zuylen

(10) Patent No.: US 10,782,477 B2
(45) Date of Patent: Sep. 22, 2020

(54) SURGICAL OPTICAL FIBER AND PROCESS OF MAKING THE SAME

(71) Applicant: AccuTech Medical Technologies Inc., Cambridge (CA)

(72) Inventor: Jeffrey Van Zuylen, Cambridge (CA)

(73) Assignee: ACCUTECH MEDICAL TECHNOLOGIES INC., Cambridge, ON (CA)

( * ) Notice: Subject to any disclaimer, the term of this patent is extended or adjusted under 35 U.S.C. 154(b) by 0 days.

(21) Appl. No.: 16/352,242

(22) Filed: Mar. 13, 2019

(65) Prior Publication Data

US 2019/0285803 A1 Sep. 19, 2019

Related U.S. Application Data

(60) Provisional application No. 62/642,912, filed on Mar. 14, 2018.

(51) Int. Cl.
*G02B 6/26* (2006.01)
*G02B 6/245* (2006.01)
*A61B 1/00* (2006.01)

(52) U.S. Cl.
CPC ............ *G02B 6/262* (2013.01); *G02B 6/245* (2013.01); *A61B 1/0017* (2013.01)

(58) Field of Classification Search
CPC ...... G02B 6/245; G02B 6/262; A61B 1/0017; A61B 2018/2266
See application file for complete search history.

(56) References Cited

U.S. PATENT DOCUMENTS

| | | | | |
|---|---|---|---|---|
| 3,779,628 A * | 12/1973 | Kapron | ................ | G02B 6/4203 385/43 |
| 4,370,021 A * | 1/1983 | Khoe | ................... | G02B 6/4203 385/33 |
| 4,688,884 A * | 8/1987 | Scifres | ................... | G02B 6/425 385/38 |
| 4,721,353 A * | 1/1988 | Khoe | ................... | G02B 6/4203 385/33 |
| 4,737,004 A * | 4/1988 | Amitay | ................ | G02B 6/2817 385/33 |
| 4,898,450 A * | 2/1990 | Jannson | ............... | G02B 6/2804 385/50 |
| 5,133,709 A | 7/1992 | Prince et al. | | |

(Continued)

FOREIGN PATENT DOCUMENTS

JP 2008-299303 12/2008

OTHER PUBLICATIONS

Canadian Intellectual Property Office as International Searching Authority, International Search Report for PCT/CA2019/050309, dated May 29, 2019.

(Continued)

*Primary Examiner* — Daniel Petkovsek
(74) *Attorney, Agent, or Firm* — Gowling WLG (Canada) LLP; Neil W. Henderson

(57) ABSTRACT

An optical fiber that includes an up taper section such that a predetermined length of the distal end of the optical fiber has a diameter that is larger than a diameter of the optical fiber at a proximal end. A portion of the optical fiber is heated to include an up taper section between the distal and proximal ends of the topical fiber.

14 Claims, 13 Drawing Sheets

(56) References Cited

U.S. PATENT DOCUMENTS

| | | | | |
|---|---|---|---|---|
| 6,330,382 | B1* | 12/2001 | Harshbarger | G02B 6/14 |
| | | | | 385/123 |
| 7,228,033 | B2 | 6/2007 | Bhagavatula et al. | |
| 7,254,298 | B2* | 8/2007 | Hatori | G02B 6/1228 |
| | | | | 385/15 |
| 7,580,609 | B1* | 8/2009 | Pannell | G02B 6/262 |
| | | | | 385/140 |
| 9,658,395 | B2 | 5/2017 | Borel et al. | |
| 2011/0178509 | A1* | 7/2011 | Zerfas | A61B 18/26 |
| | | | | 606/2.5 |

OTHER PUBLICATIONS

Canadian Intellectual Property Office as International Searching Authority, Written Opinion for PCT/CA2019/050309, dated May 29, 2019.

Espacenet, English translation of Abstract of JP2008299303A, Dec. 11, 2008.

Yu, H. et al. "Fabrication of an optical fiber micro-sphere with a diameter of several tens of micrometers" Materials, vol. 7, Issue No. 7, pp. 4878-4895, DOI:10.3390/ma7074878, Jun. 24, 2014 [online] [retrieved on May 13, 2019 (May 13, 2019)]. Retrieved from the Internet: <https://www.mdpi.com/1996-1944/7/7/4878/pdf>.

Fan, K.-C. et al. "Experimental study of fabricating a microball tip on an optical fibre", Journal of Optics A: Pure and Applied Optics, vol. 8, Issue No. 9, pp. 782-787, DOI:10.1088/1464-4258/8/9/012 Jul. 25, 2006 (Jul. 25, 2006) [online] [retrieved on May 13, 2019 (May 13, 2019)]. Retrieved from the Internet: <https://www.researchgate.net/profile/Hung-Yao_Hsu/publication/228863801_Experimental_study_of_fabricating_a_microball_tip_on_an_optical_fibre/links/09e4151308db9dce99000000.pdf>.

Wilson, C. et al. "Miniature ball-tip optical fibers for use in thulium fiber laser ablation of kidney stones" Journal of Biomedical Optics vol. 21, Issue No. 1, pp. 018003-1 to 018003-8, DOI:10.1117/1.JBO.21.1.018003 Jan. 19, 2016 (Jan. 19, 2016) [online] [retrieved on May 13, 2019 (May 13, 2019)]. Retrieved from the Internet: <https://www.spiedigitallibrary.org/journalArticle/Download?fullDOI=10.1117%2F1.JBO.21.1.018003>.

Zhou, J. et al. "Optical Fiber Tips and Their Application" Molex Technical Publication [online] [retrieved on May 13, 2019 (May 13, 2019)]. Retrieved from the Internet: <https://www.molex.com/mx_upload/superfamily/polymicro/pdfs/Optical_Fiber_Tips_and_Their_Applications_Nov_2007.pdf>.

Rego, G. "Fibre optic devices produced by arc discharges" Journal of Optics, vol. 12, Issue No. 11, pp. 113002-1 to 113002-10, DOI:10.1088/2040-8978/12/11/113002 Nov. 4, 2010 (Nov. 4, 2010) [online] [retrieved on May 13, 2019 (May 13, 2019)]. Retrieved from the Internet: <https://repositorio.inesctec.pt/bitstream/123456789/3159/1/PS-06713.pdf>.

* cited by examiner

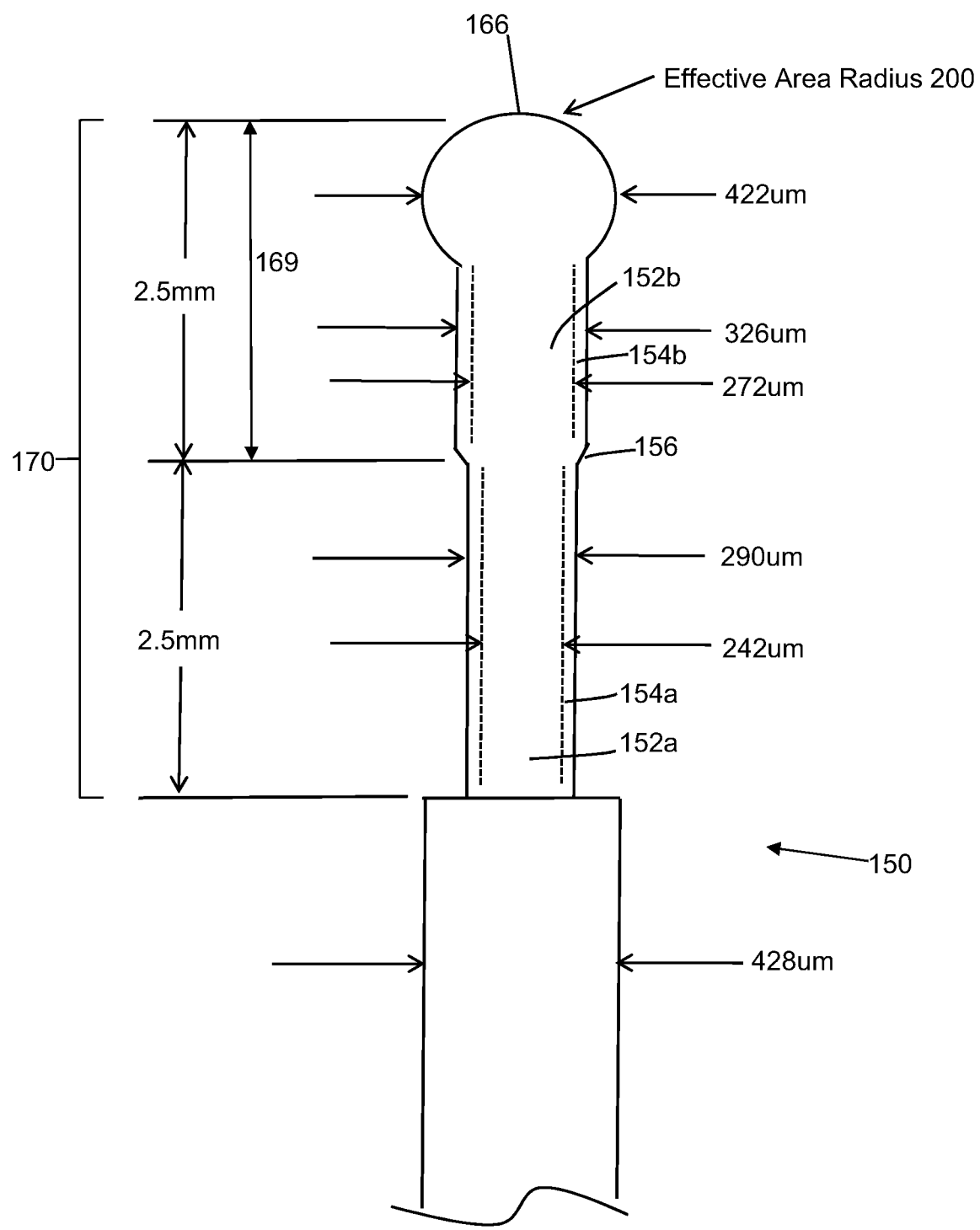

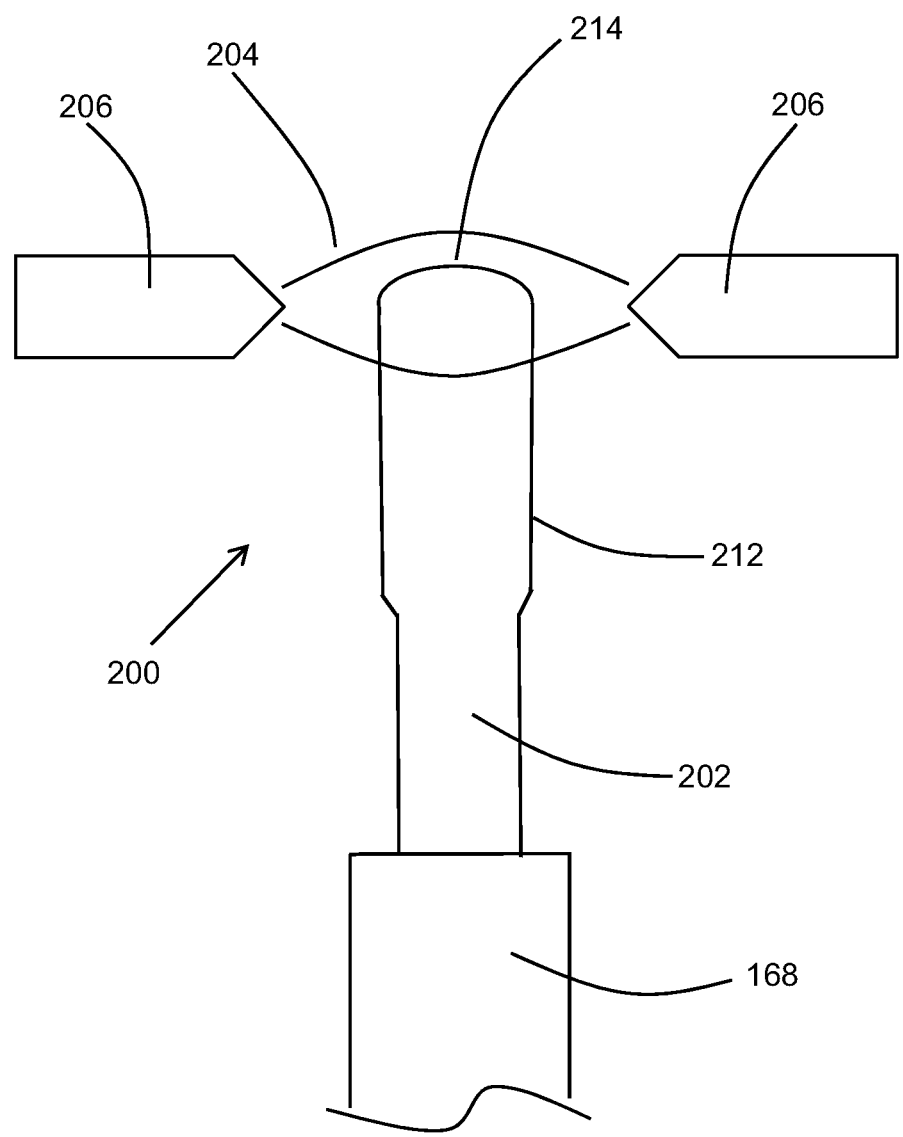

SURGICAL OPTICAL FIBER AND PROCESS OF MAKING THE SAME

CROSS-REFERENCE TO OTHER APPLICATIONS

This application claims priority from U.S. Provisional Application No. 62/642,912 filed Mar. 14, 2018 which is hereby incorporated by reference.

FIELD

The present disclosure relates generally to medical devices, and in particular, to a surgical optical fiber and process of making the same.

BACKGROUND

Fiber optic cables are often used in medical applications to deliver electromagnetic energy from an electromagnetic energy source, such as light energy from a laser source, to various clinical targets. They are typically short, in the order of a few meters, and of various diameters. When used for surgical applications they are often referred to as surgical fibers.

In one particular application, surgical fibers used for the ablation of kidney stones may connect to a 2100 nm Holmium YAG (yttrium aluminum garnet) laser as the electromagnetic energy source. The surgical fiber is passed through an ureteroscope, which was previously passed through the urethra, bladder and ureter to the inside of the kidney, which allows a distal tip of the surgical fiber to reach the targeted kidney stone.

The distal tip of a surgical fiber has traditionally been a square tip, which is created using a manufacturing process known as cleaving. Square tip surgical fibers have been recently improved by replacing the square tip with a round tip. A round tip fiber is advantageous as the sharp edges associated with a cleaved, or square tip, fiber have been removed reducing the risk of damaging the inner lining of the ureteroscope as the fiber passes through. The round tip also allows the surgical fiber to pass more easily through the ureteroscope, in particular when the scope is deflected with a sharp turn.

When the distal tip of the surgical fiber is in contact or in close proximity to the kidney stone and laser energy is activated, the distal tip will often be consumed, through erosion from contact with stone debris, by lateral fractures, or the like. This consumption of the surgical fibers is commonly referred in the medical industry as "burn back". This burn back can limit the life of the surgical fiber and may impact the effectiveness of the surgical fibre.

Therefore, there is a need for improved surgical optical fibers and process and method for making and using the same, to reduce the amount of burn back on the distal tip of surgical fibers.

SUMMARY

As described herein, there is provided a surgical optical fiber and method of making the same. In one embodiment, the fiber includes an up taper portion. The up taper portion reduces the amount of burn back on the distal tip of surgical fiber when the fiber is in use.

According to an aspect herein, there is provided an optical fiber extending between a proximal end and a distal end, the optical fiber including: a core/cladding having a predetermined first diameter; an up taper provided a predetermined distance from a distal end of the fiber, wherein the up taper comprises a sloped surface of increasing diameter around the circumference of the core/cladding; and an enlarged diameter section having a second diameter equal to the largest diameter of the up taper and the enlarged diameter section extending from the up taper to the distal end of the fiber. In some cases, the enlarged diameter section may include the up taper. In the following description, the terms up taper section and enlarged diameter section may refer to the same portion of the optical fiber, depending on context.

According to an aspect herein, there is provided an optical fiber extending between a proximal end and a distal end, the optical fiber including: a stripped section at the distal end having a first predetermined length, wherein the stripped section has the buffer and jacket removed to reveal a core/cladding of the fiber, the core/cladding having a first diameter; and an enlarged diameter section having a second diameter larger than the first diameter and the enlarged diameter section extending from the distal end for a second predetermined length along the stripped section.

In some cases, the enlarged diameter section may be configured to have a rounded distal end face having a third diameter larger than the second diameter.

In some cases, when the optical fiber is a surgical fiber, the core may include pure silica, the cladding layer may include fluorine doped silica, and the first diameter of the core/cladding may be in the range of about 200 to about 1000 μm.

In some cases, when the optical fiber is a surgical fiber, the first diameter of the core/cladding and of the first section of the distal end tip is about 290 μm with the core having a first core diameter of about 242 μm, and the second diameter of the second enlarged section of the distal end tip is about 326 μm with the core having a second enlarged core diameter of about 272 μm.

In some cases, the optical fiber disclosed herein may be for use as a surgical urology optic fiber having reduced rate of burn back compared to a surgical urology optic fiber with non-enlarged distal end tip.

In some cases, the second predetermined length may be at least 20% of the stripped/exposed portion and may alternatively be 30%, 40%, 50%, 60%, 70%, 80% of the first predetermined length.

According to another aspect herein, there is disclosed a process for enlarging a distal end of an optical fiber, the process including: removing jacket and buffer layers of the optical fiber over a first predetermined distance to expose a core/cladding layer having a first diameter; supporting the distal end of the fiber in a support frame; heating the distal end at a second predetermined distance from the distal end and moving the optical fiber or heat source until an enlarged section is formed at the distal end with a second diameter greater than the first diameter. The second predetermined distance may be at least 20% of the stripped/exposed portion and may alternatively be 30%, 40%, 50%, 60%, 70%, 80% of the first predetermined length.

In some cases, the distal end may be heated using an arc plasma created by applying a high voltage to at least two spaced apart electrodes surrounding the distal end.

In some cases, the process may further include rotating the distal end while heating the same.

In some cases, the heating step may include circumferentially applying heat about the distal end.

In some cases, the process may further include cleaving a distal portion of the enlarged section to form a distal end face defining a flat end face.

In some cases, the process may further include circumferentially heating a portion of the enlarged section at a predetermined temperature to form a distal end face defining a round face.

In some cases, the process may further include varying the temperature applied to the distal end face defining the round face to form a spherical end face, the spherical end face having a third diameter larger than the second diameter of the enlarged section.

According to another aspect herein, an optical fiber as defined herein or having an enlarged distal end obtained by the process as defined herein, is used as a surgical optical fiber, for instance during urology treatment, such as but not limited to the ablation of kidney stones.

According to yet another aspect herein, an optical fiber as defined herein or having an enlarged distal end obtained by the process as defined herein, is used as a surgical optical fiber having reduced rate of burn back compared to a surgical urology optic fiber with non-enlarged distal end tip.

According to still yet another aspect herein, there is provided a method for the ablation of a kidney stone, the method including: passing an ureteroscope through the urethra, bladder and ureter to the inside of the kidney of a patient; passing the optical fiber as defined herein or having an enlarged distal end tip obtained by the process as defined herein through the ureteroscope until the distal tip of the surgical optical fiber reached the kidney stone; and sending photoelectric energy through the optic fiber until dusting or fracturing the kidney stone.

BRIEF DESCRIPTION OF THE DRAWINGS

Further features and exemplary advantages will become apparent from the following detailed description, taken in conjunction with the appended drawings, in which:

FIG. 6 is a schematic plan view of another embodiment of a distal end of an optical fiber having a enlarged section;

FIG. 7C is a schematic plan view of the distal end of an optical fiber during the manufacturing of a round tip on the enlarged section using arc plasma;

DESCRIPTION OF THE EMBODIMENTS

The disclosure is directed at an optical fiber and process of making the same. In one embodiment, the optical fiber includes a tapered, up taper, or enlarged section near a distal end of the optical fiber.

In one embodiment, the optical fiber and method disclosed herein generally includes enlarging the diameter of the distal tip of the optical fiber using for example an up taper or enlarged section of the tip. The up taper may be configured such that the diameter of the core/cladding (sometimes referred to as the "glass rod" or "glass fiber") increases from its nominal diameter to a larger diameter over a defined distance. The enlarged section or up taper may start at some predetermined distance from the jacket of the fiber and extend to the distal end face of the tip which can be flat, round or spherical. Preferably, the distal end face of the fiber will be round or spherical, the diameter of which will be greater due to the presence of the up taper compared to a current fibers without up taper.

The present disclosure also relates to a process, using for example, an arc plasma technique, for increasing the diameter of the optical fiber and adding the up taper/extended diameter section. By controllably heating the distal tip of the glass rod with the arc plasma, the glass rod will expand in size. Once the desired size has been obtained, the location of the arc can be moved further along the glass rod where a new section of the glass rod may be enlarged. This process may be repeated until the diameter of the glass rod is enlarged over a predetermined distance. Once the diameter of the glass rod has been enlarged, the distal enlarged tip may be cleaved to produce a flat end face, or further heated to form a round or ball (spherical) end or tip. This is described in more detail below.

When used in surgical applications, the tapered section reduces the amount of burn back experienced, such as, but not limited to, when it is used in the ablation of kidney stones. Although the present embodiments are described with regard to use for surgical treatments, the optical fibers described herein can be used for other applications such as, but not limited to, lighting applications, high power industry cutting/welding/engraving, or the like.

The term "about" is used in the present disclosure to mean that the value or data associated with this term (such as a length) may vary within a certain range depending on the margin of error of the method or device used to evaluate or measure such value or data. A margin or variation of up to about 10% is typically accepted to be encompassed by the term "about". Also, the range may also be one that would be understood by one skilled in the art.

Figure 1:
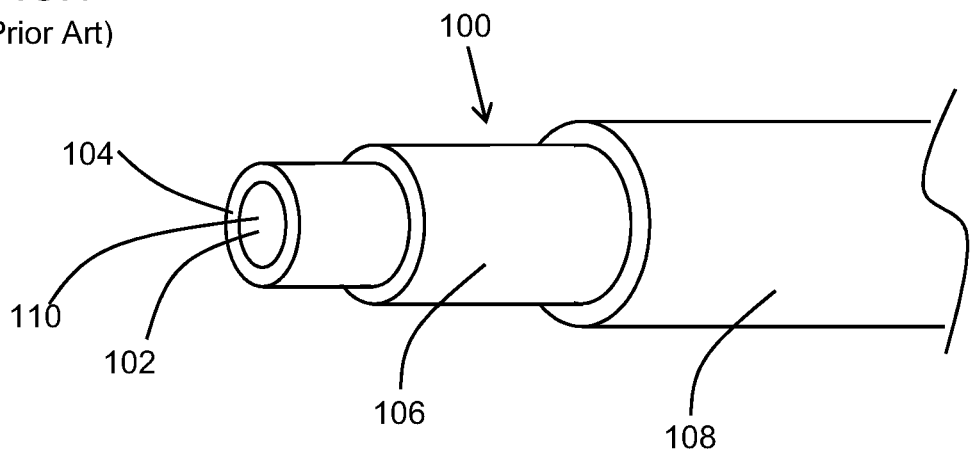
FIG. 1 is a schematic perspective view of a distal end of a prior art optical fiber.

Turning to FIG. 1, a perspective view of a prior art optical fiber is shown. Typically, the optical fiber 100 includes a core, or core layer, 102 and a cladding, or cladding layer, 104 circumferentially disposed about the core 102. These may be seen as a core and cladding combination. In general, the core and the cladding are seen as a single rod of glass and the two components cannot generally be readily separated from one another. The fiber 100 may also include a buffer layer 106 circumferentially disposed about the cladding layer 104 and a jacket layer 108 circumferentially disposed about the buffer layer 106.

In general, the cladding 104 in an optical fiber has a lower refractive index than the core 102 causing the light to be confined to the core 102 of the optical fiber 100 by total internal reflection at the boundary between the two layers 102 and 104. For surgical optical fibers, the core 102 is typically made with pure silica, or pure silica glass, with a diameter typically in the range of about 200 to 1000 μm, and the cladding 104 is made with fluorine doped silica. The buffer layer 106 is generally made with an acrylate and the jacket layer 108 is typically made with a polymeric material such as, but not limited to, Tefzel™ (modified ETFE: ethylene-tetrafluoroethylene fluoroplastic). Other materials known in the art of optical fiber manufacturing may also be used. The length of surgical fibers used for applications in urology is typically about three (3) meters.

In FIG. 1, a distal end 110 of the optical fiber is shown. The distal end 110 will be described in more detail below. A proximal end (not illustrated) of the optical fiber, when used as a surgical fiber, is typically terminated with a specialized connector system, known as a Sub Miniature A (SMA), which includes a ferrule and nut in order to secure and align the surgical fiber with a laser system or electromagnetic energy source, however, other connectors may also be contemplated.

Figure 2:
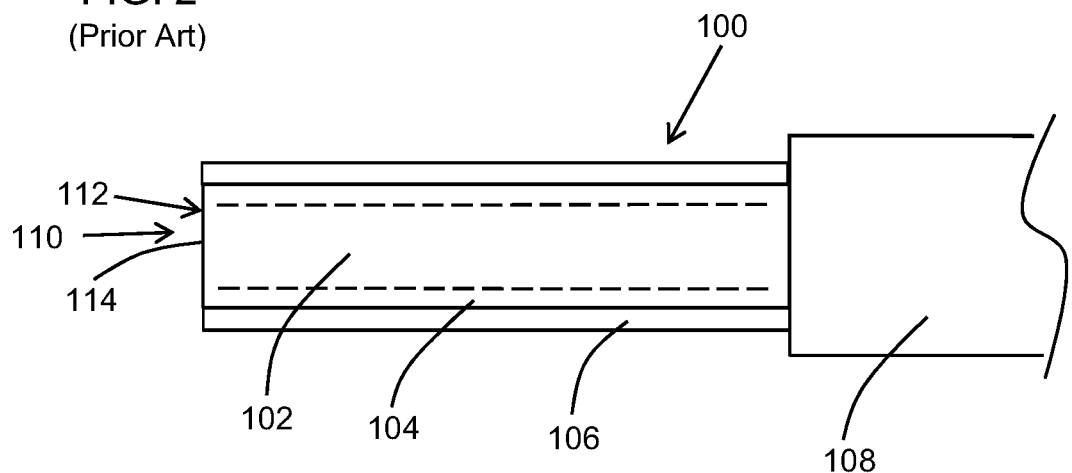
FIG. 2 is a schematic plan view of a distal end of a prior art optical fiber with a cleaved tip.

Turning to FIG. 2, a perspective view of a prior art configuration for a distal tip of a surgical fiber is shown. As can be seen in FIG. 2, the optical, or surgical, fiber 100 is shown wherein the jacket layer 108 has been removed a predetermined distance from a distal tip 112, which in the current embodiment is a square distal tip 114. In one embodiment, the jacket layer 108 is removed over a distance of about 5 mm.

For a surgical fiber having a square distal tip, the buffer 106 typically remains intact about the cladding layer 104. Square tip fibers, such as the one illustrated on FIG. 2, are produced by a method known as cleaving and result in a smooth, flat and square surface at a distal end 110 of the fiber 100.

Figure 3:
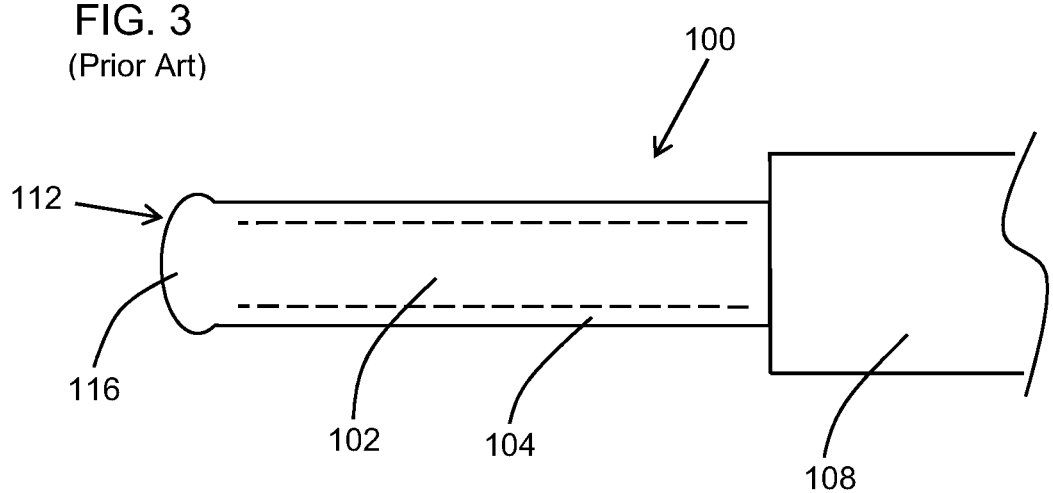
FIG. 3 is a schematic plan view of a distal end of a prior art optical fiber with a round tip.

For surgical fibers having a round distal tip, such as the one illustrated in FIG. 3, the buffer layer 106 is also removed with the jacket layer 108. Round tip fibers are typically made by melting the distal tip of the fiber to form a round tip. The round tip profile can vary from a slight contour to a ball/spherical shape. The heat used to create the round tip will typically burn off the buffer layer 106, or coating, thus the buffer 106 is generally removed prior to the process in order to reduce or minimize any burning or contamination of the glass rod.

The purpose of the buffer is generally to protect the glass rod (core/cladding combination) from fracture. With the buffer layer 106 removed, as is the case with round tip fibers, the probability of fracture in contact with a kidney stone or the like is increased, particularly when under laser power. A fracture will, in turn, generally increase the rate of burn back. Furthermore, the rate of burn back is inversely proportional to the fiber diameter, meaning as the fiber diameter decreases, the rate of burn back increases. In particular, the small core fiber at, for example, a core diameter of 242 μm, exhibits a high rate of fractures, resulting in a high burn back rate which is undesirable for clinical applications, in particular the ablation of kidney stones.

Figure 4:
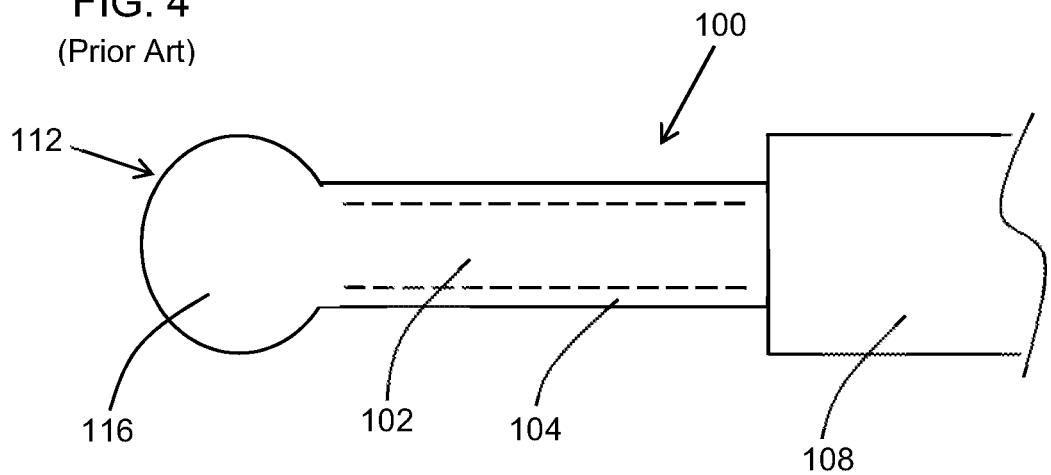
FIG. 4 is a schematic plan view of a distal end of a prior art optical fiber with a ball tip.

In one embodiment, both layers are typically removed over a distance of about 5 mm. In the current prior art optical fiber 100, the optical fiber includes a round distal tip 116. Round tip fibers are typically made using a plasma arc which, when combined with a controlled process, will at least partially melt the tip of the core layer 102 and cladding layer 104 to form the round distal tip 116. The profile of the round distal tip 116 may vary from a very slight contour as illustrated in FIG. 3 to a ball or sphere shape as illustrated in FIG. 4.

Figure 5:
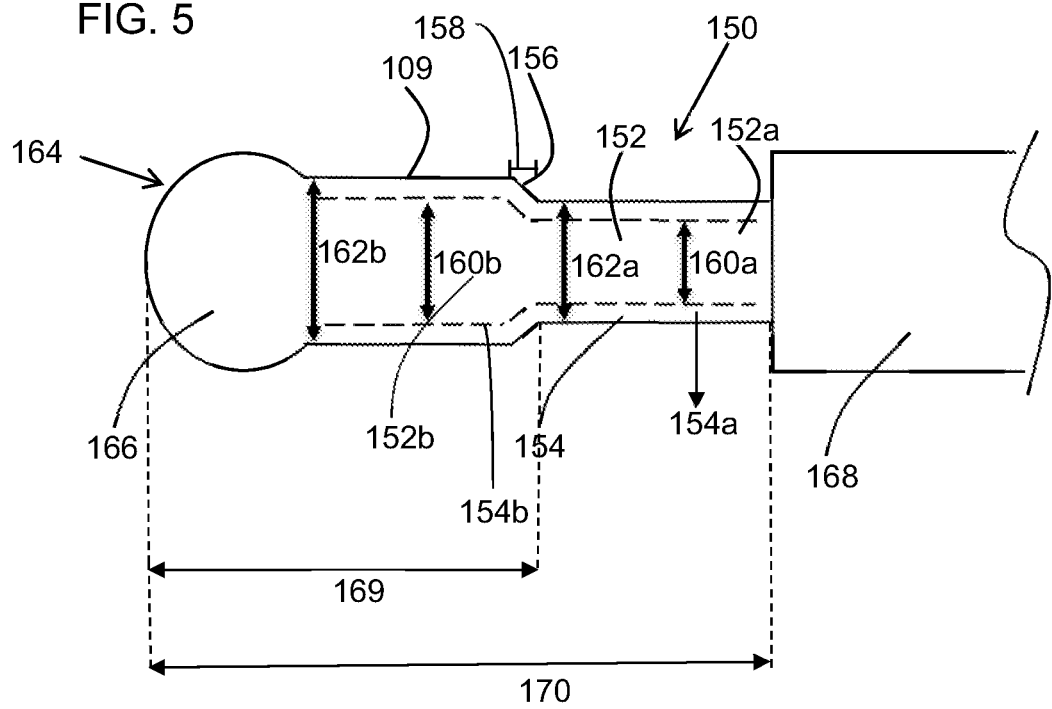
FIG. 5 is a schematic plan view of a first embodiment of a distal end of an optical fiber with an enlarged section in accordance with an embodiment herein.

Turning to FIG. 5, a perspective view of the distal end of a surgical fiber according to an embodiment of the disclosure is shown. In the current embodiment, the optical, or surgical fiber, 150 includes a core layer 152 and a cladding layer 154 such as described above. The core layer 152 includes a first core section 152a and an enlarged core section 152b while the cladding layer 154 includes a first cladding section 154a and an enlarged cladding section 154b. A taper section, or an up taper, 156 connects the first sections 152a, 154a and the enlarged sections 152b, 154b of the core layer 152 and the cladding layer 154. The up taper 156 may be seen as a sloped surface that causes the diameter of the core layer and cladding layer to increase or enlarge between the first and enlarged sections at the distal end of the optical fiber 150. As can be seen, a diameter 160a of the core 152 in the first core section 152a is less than a diameter 160b of the core 152 in the enlarged core section 152b and a diameter 162a of the cladding 154 in the first cladding section 154a is less than a diameter 162b of the cladding 154 in the enlarged cladding section 154b. In a preferred embodiment, the diameters 160b and 162b are equal to a largest diameter of the up taper 156. In another embodiment, the up taper 156 is applied to the core and cladding combination over a predetermined distance 158. In another embodiment, the enlarged sections 152b and 154b may include the up taper 156. In the current disclosure, the terms up taper section and enlarged section may refer to the same portion of the optical fiber, depending on context.

The up taper 156 will generally be provided over a predefined distance from the distal end 164 (or distal tip) of the optical fiber 150, in this case, a round tip 166. In some cases, the up taper 156 may refer to either or both of the areas of increasing diameter or to the section of the fiber 150 having the increased diameter. By increasing the diameter of the core and cladding layers near the distal end 164, the rate of burn back can be reduced. In an embodiment, the up taper/extended or enlarged diameter section 169 is at least approximately half (50%) of the portion of the distal end/tip where the buffer (not shown) and/or jacket 168 have been removed (seen as 170). Generally speaking, the up taper section should be made as long as practically possible.

In another specific embodiment, as schematically illustrated on FIG. 6, a surgical fiber 150 includes a first core section 152a with a 242 μm diameter and a first cladding section 154a with a 290 μm diameter. Via the up taper 156, the diameter of the enlarged core section 152b is increased to a 272 μm diameter and the diameter of the enlarged cladding section is increased to a 326 μm diameter. In the current embodiment, the ball tip 166 has an effective area radius 200 and/or a diameter of about 422 μm.

In one embodiment, the portion of the fiber 150 that has the buffer/jacket removed ("exposed portion" 170) is about 5 mm long and the up taper/enlarged section including the end ball tip 166 is about 2.5 mm long (i.e. approximately half (or 50%) of the exposed portion of the surgical fiber). In another embodiment, the exposed portion 170 is about 5 mm long and the up taper/enlarged section is about 3 mm long (i.e. approximately 60% of the exposed portion). In some embodiments, the portion of the fiber 150 with the buffer/jacket removed may be more or less than 5 mm. In these cases, the enlarged diameter section is preferably approximately half of the exposed portion. However, in cases where the exposed portion is longer, it may be beneficial to make the enlarged diameter section longer than half of the exposed portion as long as the heating to provide the enlarged diameter section does not affect the edge of the buffer and/or jacket that has been removed. In some cases, a beneficial effect can be obtained by having the enlarged diameter section be a percentage of the exposed portion, for example, 20%, 30%, 40%, 50%, 60%, 70%, 80% or some percentage within this overall range depending on the size of the exposed section and the amount of reduction in burn-back required.

Laboratory testing demonstrated that the rate of burn back with this embodiment (with the up taper and enlarged section 169 being about 50% of the exposed portion 170) is reduced by approximately five (5) times compared with conventional approaches.

Figure 7A:
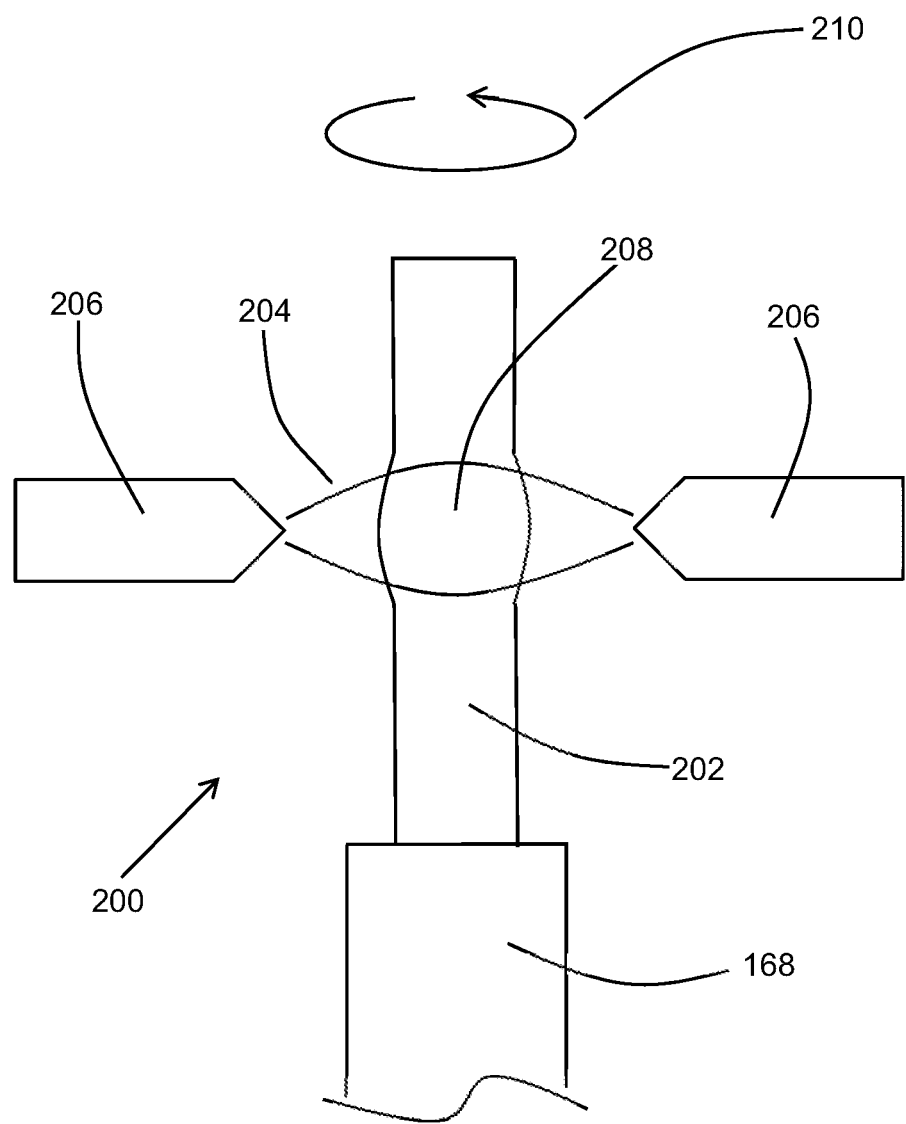
FIG. 7A is a schematic plan view of the distal end of an optical fiber during the manufacturing of an up taper using arc plasma.
Figure 7B:
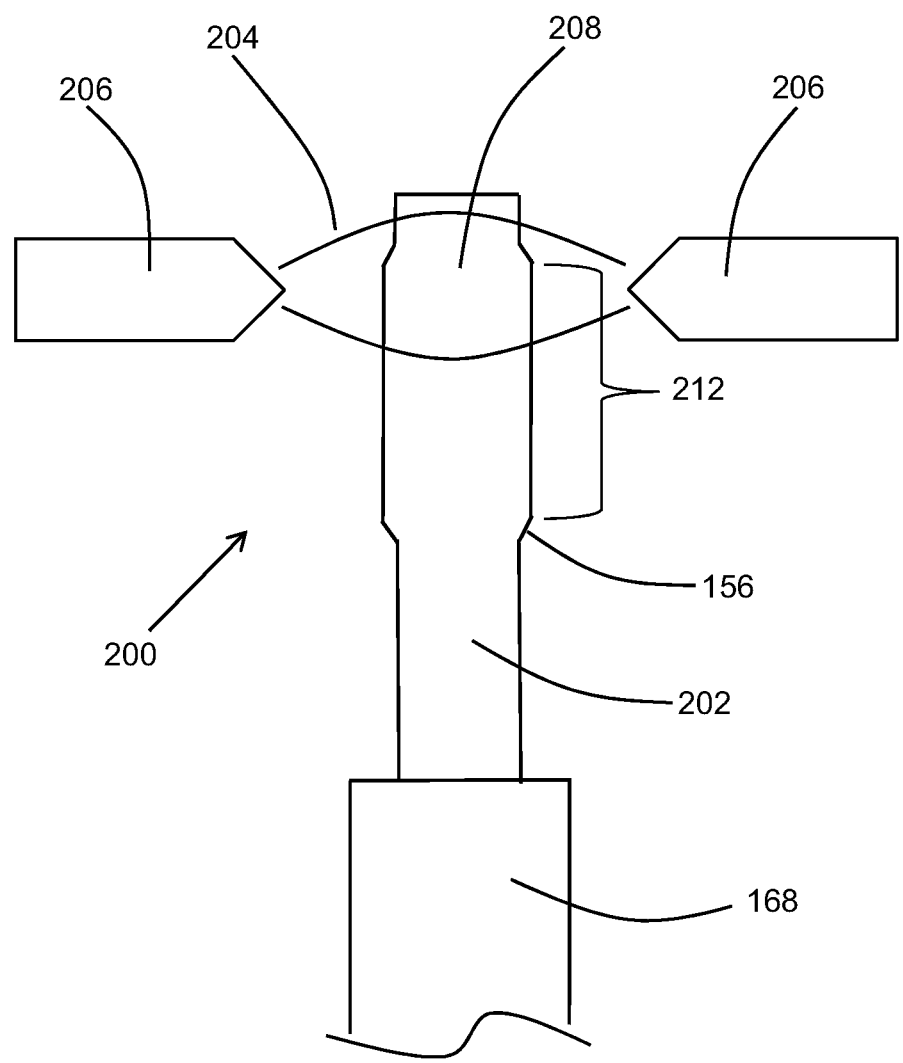
FIG. 7B is a schematic plan view of the distal end of an optical fiber during the manufacturing of the enlarged section using arc plasma.

In one embodiment, the up taper can be made using a heating process. This is schematically shown in FIG. 7A. As shown, the optical, or surgical, fiber 200 includes a core layer and a cladding layer which may be seen as a core and cladding combination 202. An arc plasma 204, which may be created by applying a high voltage to a set of spaced electrodes 206, heats the core and cladding combination 202. In the current embodiment, the set of spaced electrodes 206 includes two (2) electrodes, however, other numbers, such as three (3) or more are also contemplated. By controlling the arc plasma in bursts and intensity, the core and cladding combination 202 can be heated near or to its melting temperature to increase a diameter of the core and cladding combination 202. In one embodiment, gravity and/or surface tension will then cause the core and cladding combination 202 to expand in size (such as at 208) where the arc plasma 204 contacts the fiber 200. Rotating the fiber 200, such as in the direction of arrow 210, during the plasma arc process, may help with distributing the heat more evenly throughout the core and cladding combination 202. In another embodiment, the electrodes 206 may be rotated about the fiber 200. Once a desired size or enlarged diameter has been obtained, the arc plasma 204 can be moved and relocated further along the core and cladding combination 202 where a new section of the glass, or optical fiber 200, may be enlarged. This process may be repeated until a desired or predetermined length 212 of the glass, or optical, fiber is enlarged as illustrated in FIG. 7B. Once the predetermined length 212 of the core and cladding combination 202 has been enlarged, the distal tip may be created such as the round distal tip 214 as illustrated in FIG. 7C. In one embodiment, the arc plasma 204 can be shifted toward the distal end of the fiber 200 to generate the distal tip. As will be understood, although a rounded tip is shown, the distal tip may also be a square tip or a ball shape tip.

Figure 8:
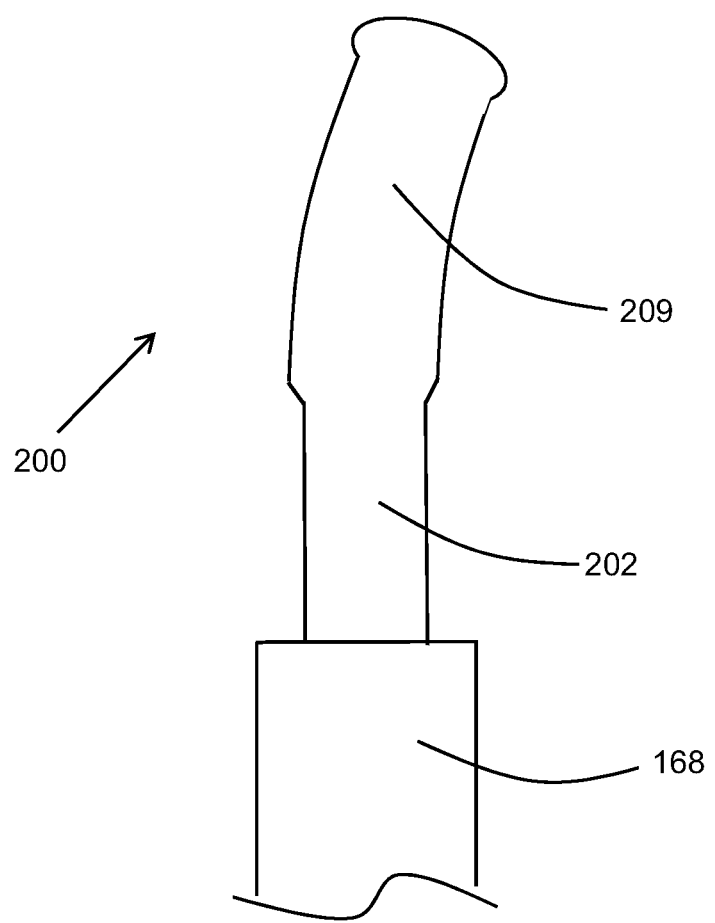
FIG. 8 is a schematic plan view of a distal end of an optical fiber with a bend off axis.

In order to keep the fiber 200 straight throughout the heating process of the enlarged section over the predetermined distance 212, the system may include an alignment apparatus. Uneven heating and uneven orientation are two examples of factors which could cause the fiber 200 to bend off axis, as illustrated by 209 in FIG. 8. Rotating the fiber 200 (as illustrated by the arrow 210 in FIG. 7A) during the application of the arc plasma 201 may help reduce bending but may not be sufficient to counteract all bending effects.

Figure 9:
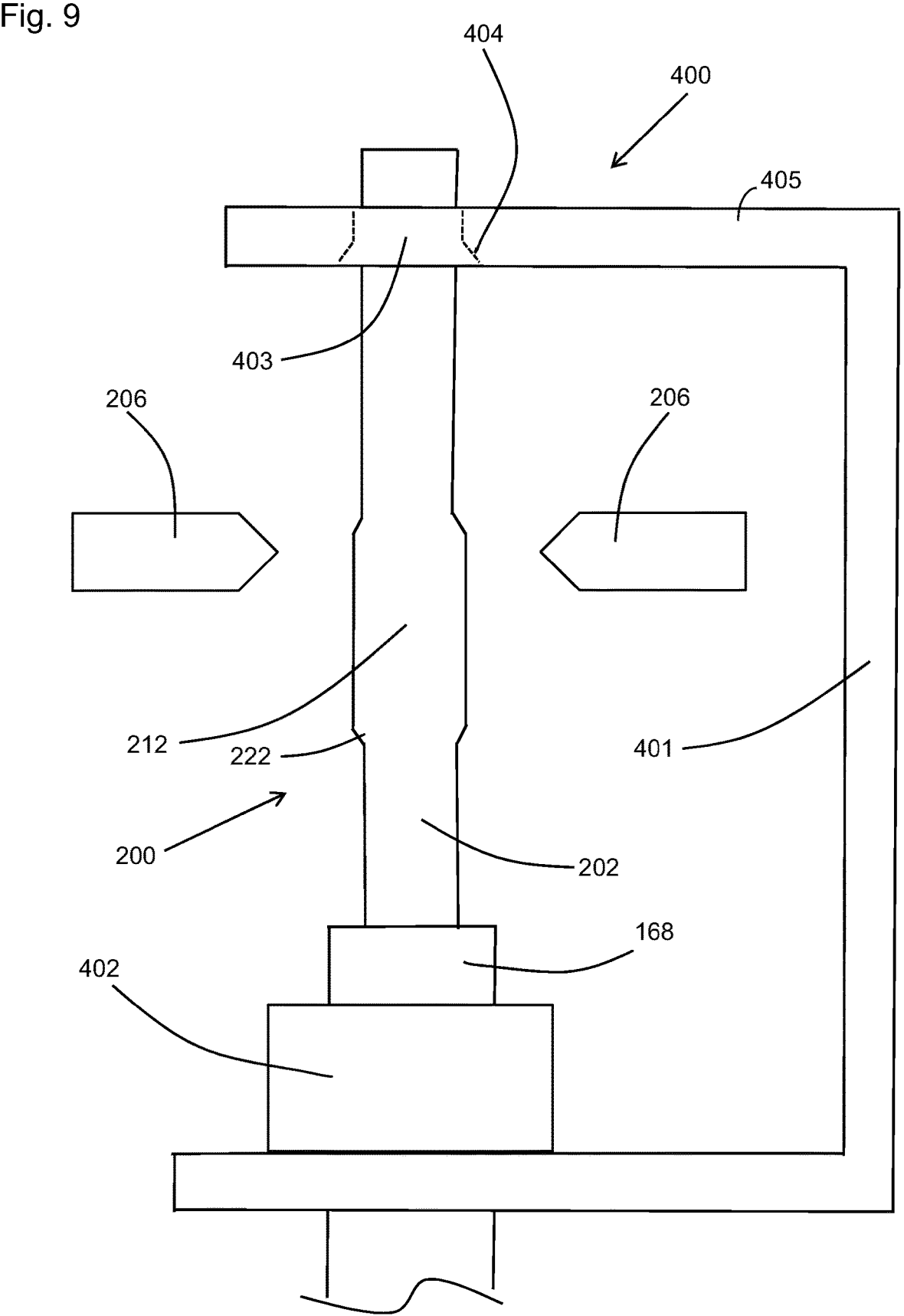
FIG. 9 is a schematic plan view of the distal end of an optical fiber maintained in a process fixture during manufacturing using arc plasma.

In order to provide further alignment of the fiber relative to the center of the arc plasma 204, the fiber 200 can be preferably supported with a supporting system 400 as schematically shown in FIG. 9. The supporting system 400 may include a fixture 401 disposed vertically on either side of the set of electrodes 206 to maintain the fiber 200 in a straight configuration during the process of applying the arc plasma 204 to create the up taper 222. Although shown in space for clarity, the set of electrodes may be mounted to the fixture 401. In the current embodiment, the fiber 200 may be held in place below the electrodes 206, using, for instance a clamp 402, such as a clamping V groove holder, and held above the electrodes 206 by a plate or bracket 405 including a hole 403 having an appropriate size to receive the distal end of the fiber. In one embodiment, the plate or bracket may also include a funnel shape 404 leading to the hole 403 in order to help guide the distal end of the fiber through the hole 403.

Figure 10A:
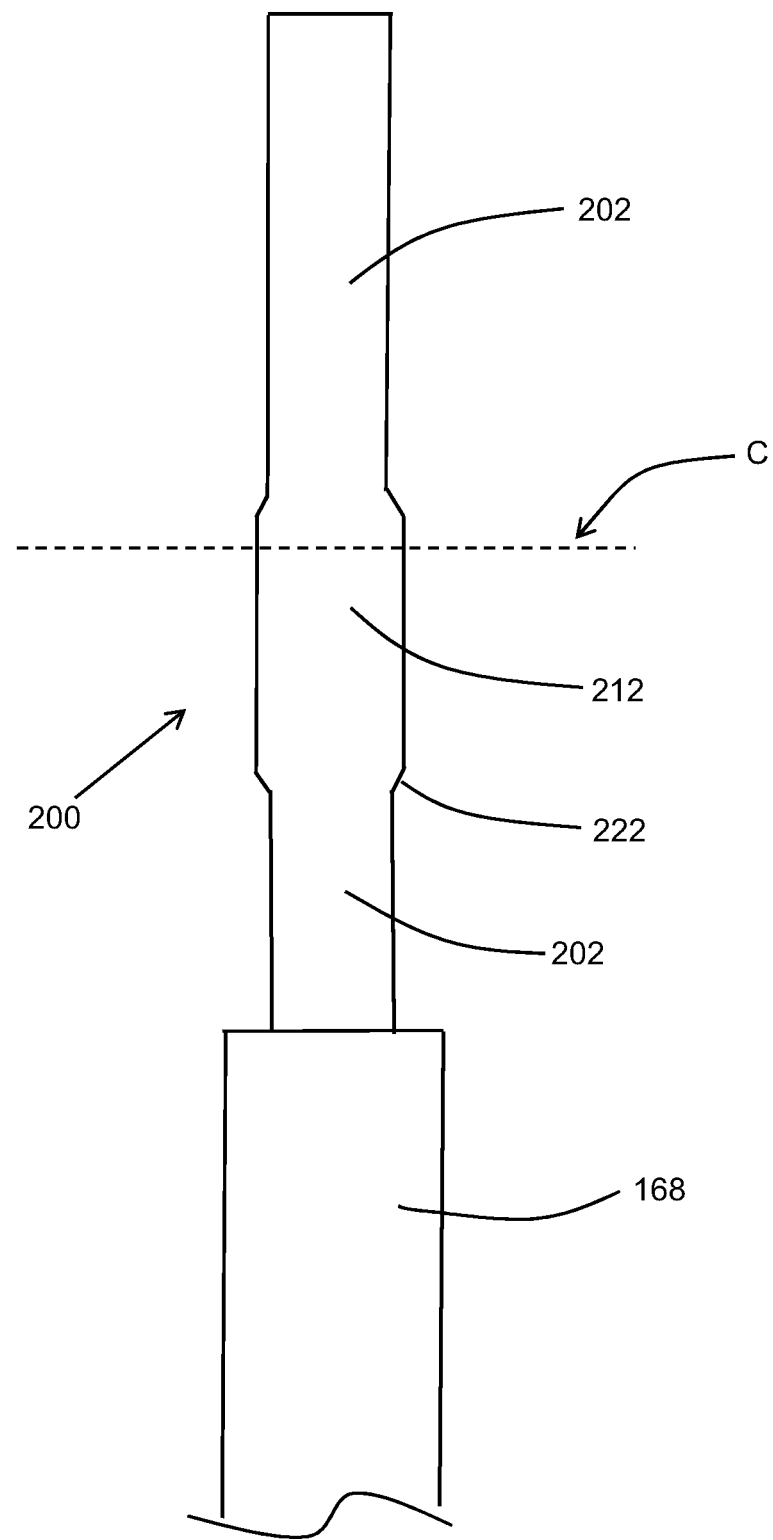
FIG. 10A is a schematic plan view of the distal end of an optical fiber after the manufacturing of the enlarged section.
Figure 10B:
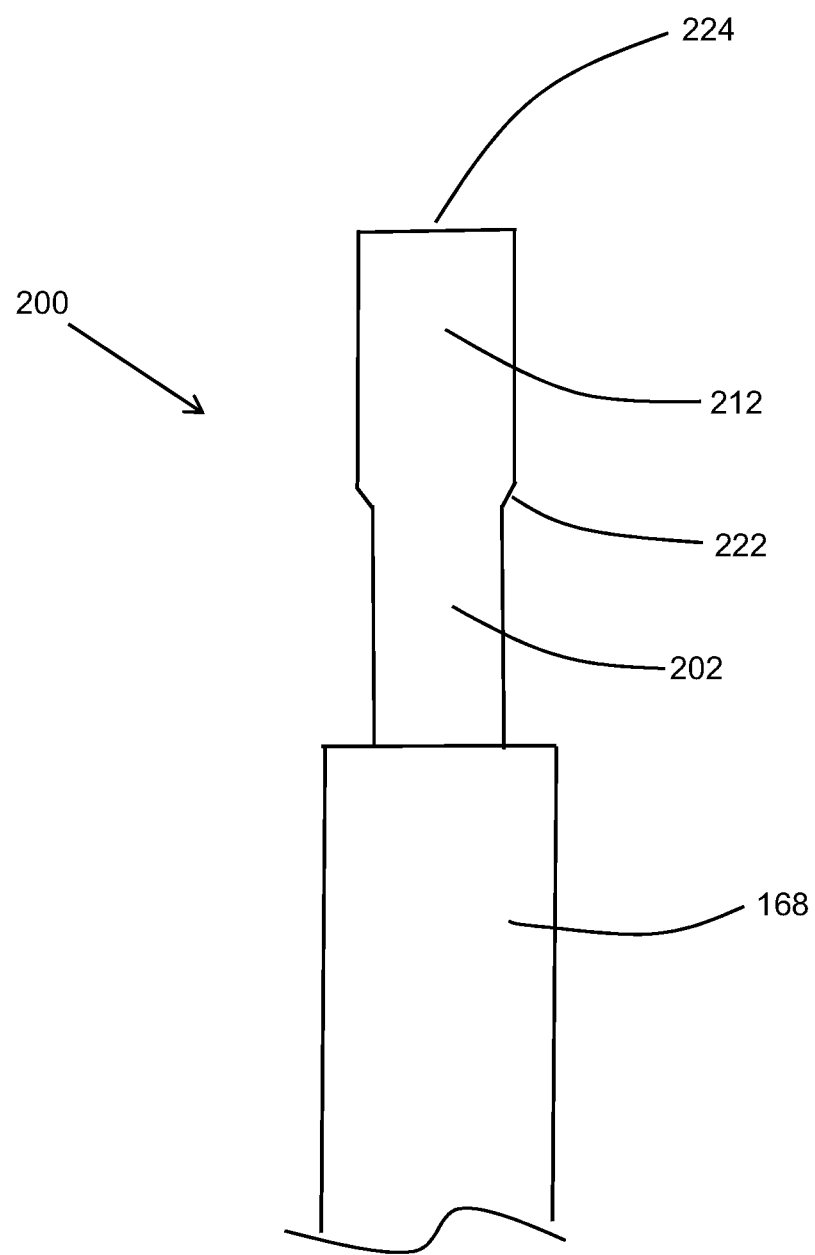
FIG. 10B is a schematic plan view of the distal end of the optical fiber of FIG. 10A after cleaving.
Figure 10C:
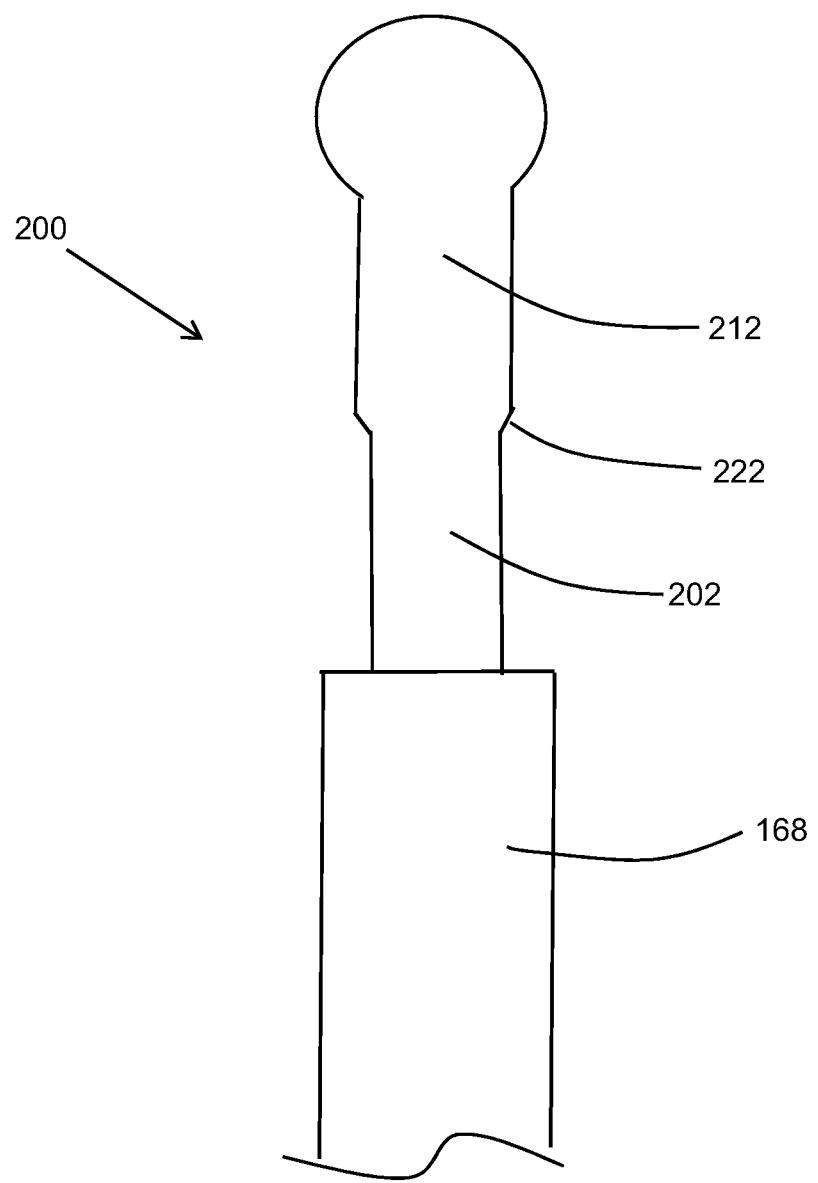
FIG. 10C is a schematic plan view of the distal end of the optical fiber of FIG. 10B with the addition of a round tip.

In some embodiments, once a section of the core and cladding combination 202 has been enlarged, the straight distal end, or tip, of the surgical fiber 200 may appear as illustrated in FIG. 10A. In these embodiments, the enlarged section 212 may be cleaved (dotted line C on FIG. 10A) using a standard cleaving process. A cleaved end 224 of the enlarged portion 212 of the core and cladding combination 202 may then configured as a square distal tip (FIG. 10B) or can then be configured with a round distal tip (FIG. 10C).

Figure 11:
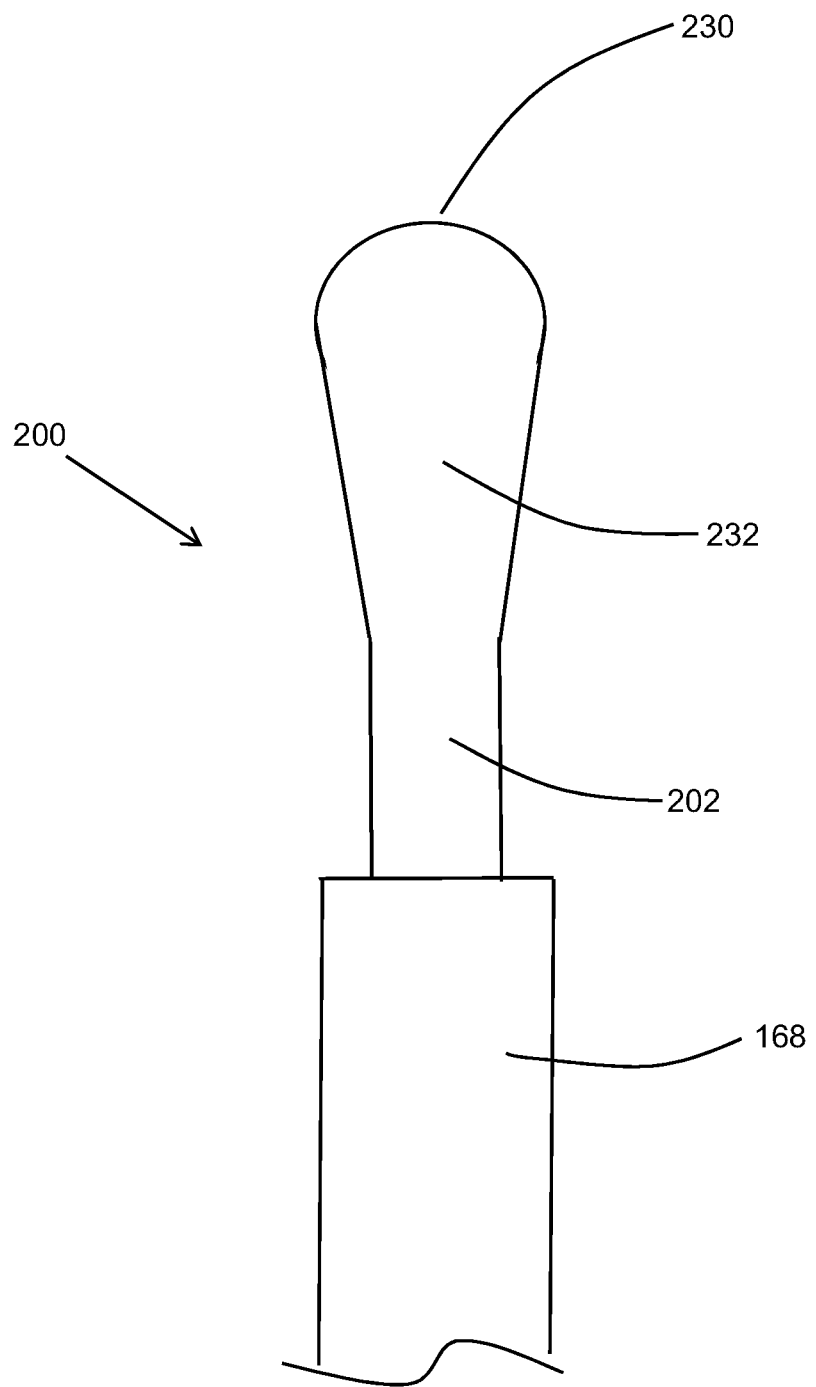
FIG. 11 is a schematic plan view of the distal end of an optical fiber having an up taper section ended by a round tip.

FIG. 11 shows another embodiment where the surgical fiber 200 includes a distal tip 230 that is configured to have an expanding diameter section 232 that has an increasing diameter starting from the nominal, or first, diameter of the first core section and first cladding section to a larger diameter over a predetermined distance until reaching the larger diameter where the spherical round distal tip 230 is added. In other words, the up taper/enlarged diameter section could be configured such that the diameter of the glass rod increases from its nominal diameter to a larger diameter over a predetermined distance. In the current embodiment, the up taper section and the enlarged diameter section may be seen as the same.

Figure 12:
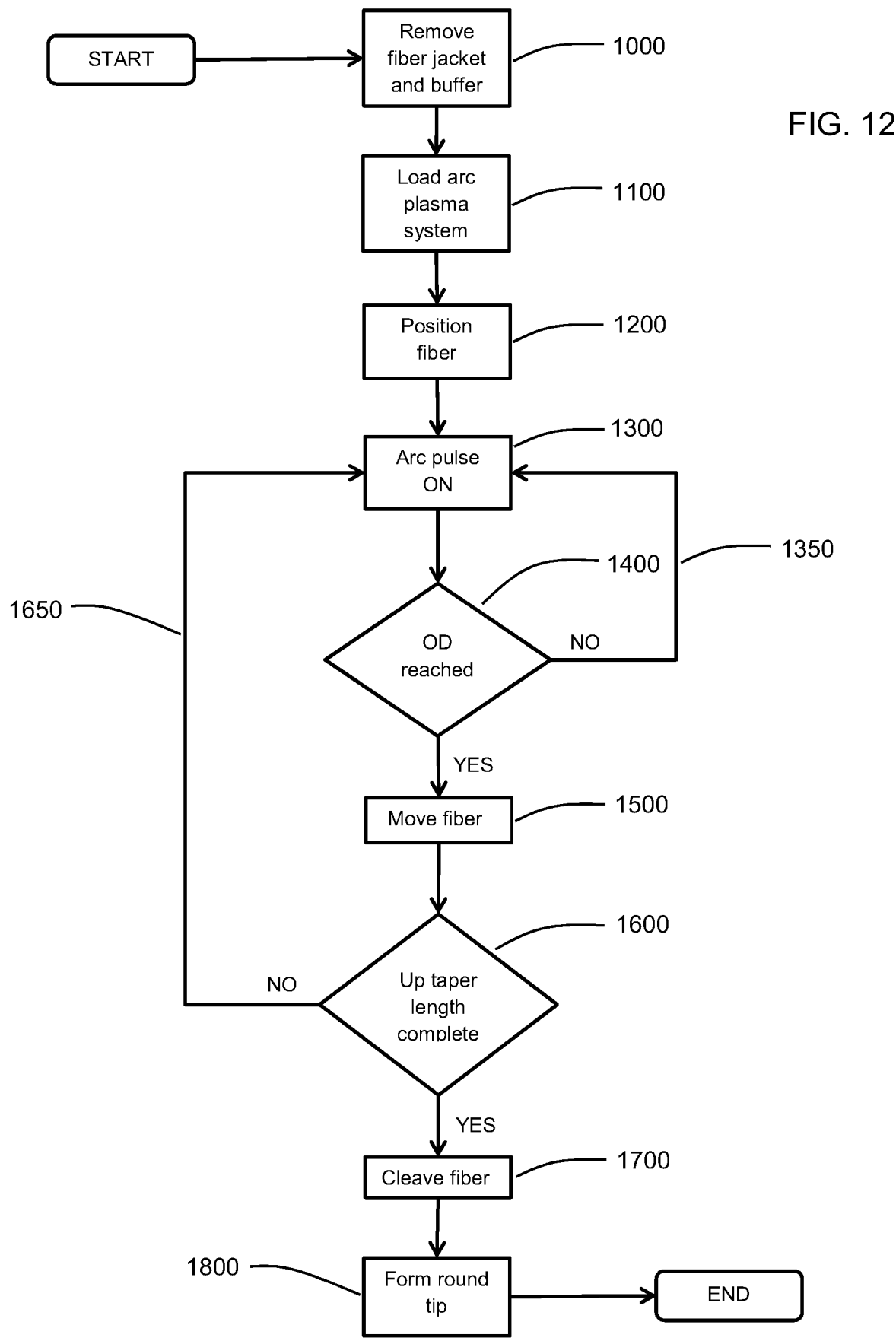
FIG. 12 is a flowchart illustrating an embodiment of a manufacturing process of an optical fiber, in accordance with an embodiment herein.

Turning to FIG. 12, a flowchart illustrating one embodiment of a manufacturing process of an optical, or surgical, fiber in accordance with an embodiment is shown.

As indicated above, the fiber jacket layer and buffer layer are removed from the distal end of the fiber 1000. In some embodiments, only the jacket layer may be removed. The jacket layer, or the jacket layer and the buffer layer, are preferably removed a predetermined distance from the distal end of the fiber. The optical fiber is then loaded into a heating system, such as an arc plasma system 1100. In one embodiment, the optical fiber is positioned 1200 into the arc plasma system such as schematically shown in FIG. 9. As previously described, the fiber is preferably kept straight in the arc plasma system by the supporting system.

The fiber is then heated by controlling (for example, pulsing) the arc plasma 1300. A check is performed to determine if an appropriate, or desired diameter (OD) is reached 1400. If the OD is not reached, the heating of the fiber via arc pulsing continues, or is repeated, 1300. In some cases, the diameter may be measured and in others, the diameter may be approximate based on heating time/intensity or the like. Once it is determined that the OD for that section is reached, the fiber is shifted 1500 to move the heating position along the distal tip until it is determined that a given, predetermined, or desired, up taper length (or enlarged diameter section length) is complete, or produced 1600. If the enlarged diameter section length is not complete, the heating/measuring/moving of the fiber is repeated 1650 until it is determined that the up-taper section (enlarged diameter section) is completed. The fiber is then cleaved 1700 and a distal tip such as a round tip may be formed 1800 at the distal end of the fiber. In some other cases, the round tip may be formed at the distal end of the optical fiber without cleaving.

In general, optical fibers having the features herein may have applications where different physical and optical properties are desired in one fiber such as high flexibility with a thin fiber and larger beam diameter with a large fiber. In some cases, optical fibers having the features herein can be considered a hybrid fiber, combining two different sized fibers of which both have inherent advantages, thin for flexibility and thick for larger beam diameter. In particular, embodiments herein provide for a larger diameter fiber (having a larger beam diameter) at the distal end, which will allow a larger area of a kidney stone to be irradiated, reducing the amount of time required to break or dust the kidney stone. A large beam diameter will also generally be less prone to drilling through the stone rather than breaking it into fragments or dust. At the same time, embodiments herein provide the benefit of a thinner diameter fiber over the remainder of the fiber. This allows for greater flexibility when physically flexing the ureteroscope to move within the body.

In the preceding description, for purposes of explanation, numerous details are set forth in order to provide a thorough understanding of the embodiments. However, it will be apparent to one skilled in the art that other arrangements and embodiments would be feasible.

The above-described embodiments are intended to be examples only. Alterations, modifications and variations can be effected to the particular embodiments, including selecting elements from each embodiment for use with others or removing some elements from particular embodiments, by those of skill in the art without departing from the scope of the application, which is defined solely by the claims appended hereto.

I claim:

1. A surgical optical fiber comprising:
   a core and cladding combination, the core and cladding combination including a distal end and a proximal end and comprises;
      a first core section having a first core diameter and an enlarged core section having an enlarged core diameter;
      a first cladding section having a first cladding diameter and an enlarged cladding section having an enlarged cladding diameter; and
      an up taper section connecting the first core section to the enlarged core section;
   wherein the enlarged core diameter is greater than the first core diameter and the enlarged cladding diameter is greater than the first cladding diameter; and
   wherein the core and cladding combination is enlarged in diameter at the distal end of the core and cladding combination with respect to the proximal end; and
   an expanded tip, connected at the distal end of the core and cladding combination.

2. The surgical optical fiber of claim 1 further comprising:
   a buffer layer circumferentially disposed about the cladding layer; and
   a buffer layer circumferentially disposed about the buffer layer.

3. The surgical optical fiber of claim 2 wherein the fiber further comprises:
   a stripped section at the distal end having a first predetermined length,
   wherein the stripped section has the buffer and jacket removed to reveal the core and cladding combination of the fiber; and
   the enlarged diameter section extending from the distal end for a second predetermined length along the stripped section.

4. The surgical optical fiber of claim 3 wherein the second predetermined length is at least 20% of the stripped/exposed portion.

5. The surgical optical fiber of claim 2 wherein the enlarged distal end is obtained by a process comprising:
   removing the jacket and buffer layers of the optical fiber over a first predetermined distance to expose core and cladding combination;
   supporting the distal end of the fiber in a support frame;
   heating the distal end at a second predetermined distance from the distal end and moving the optical fiber or heat source until an enlarged section is formed at the distal end with a second diameter greater than the first diameter.

6. The surgical optical fiber of claim 2 wherein the jacket layer is removed over a distance of approximately 5 mm.

7. The surgical optical fiber of claim 1 wherein the expanded tip is selected from the group comprising: a square tip, a round tip and a ball shaped tip.

8. The surgical optical fiber of claim 1 wherein
   the cladding section is circumferentially disposed about the core section.

9. The surgical optical fiber of claim 8 wherein the core section is pure silica and the cladding section is fluorine doped silica.

10. The surgical optical fiber of claim 1 where a length of the enlarged core section is at least 50% of a length of the enlarged core section and first core section combined.

11. The surgical optical fiber of claim 1 wherein the fiber is configured for use as a surgical urology optic fiber having reduced rate of burn back.

12. The surgical optical fiber of claim 1 wherein the first diameter of the core and cladding combination is in the range of about 200 to about 1000 μm.

13. The surgical optical fiber of claim 1 wherein the expanded tip has a rounded end face having a third diameter larger than the second diameter.

14. The surgical optical fiber of claim 1 wherein the first diameter of the core and cladding combination and of the first section of the distal end is about 290 μm with the core having a first core diameter of about 242 μm, and the second diameter of the second enlarged section of the distal end is about 326 μm with the core having a second enlarged core diameter of about 272 μm.

* * * * *